(12) United States Patent
Williams

(10) Patent No.: US 10,213,205 B2
(45) Date of Patent: Feb. 26, 2019

(54) T-SLOT TILT ANVIL FOR CIRCULAR STAPLING INSTRUMENT

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 1091 days.

(21) Appl. No.: 13/888,500

(22) Filed: May 7, 2013

(65) Prior Publication Data
US 2014/0008413 A1 Jan. 9, 2014

Related U.S. Application Data

(60) Provisional application No. 61/668,540, filed on Jul. 6, 2012.

(51) Int. Cl.
A61B 17/115 (2006.01)
A61B 17/072 (2006.01)

(52) U.S. Cl.
CPC . *A61B 17/1155* (2013.01); *A61B 2017/07257* (2013.01)

(58) Field of Classification Search
CPC ...... A61B 17/1155; A61B 2017/07257; A61B 2017/07214; A61B 17/068; A61B 2017/2927; A61B 2019/4857; A61B 2017/00473; A61B 17/115
USPC .................................................. 227/8, 175.2
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

European Search Report dated Jun. 25, 2015 (received Jul. 28, 2015), issued in European Application No. 13175228.9.

(Continued)

*Primary Examiner* — Michelle Lopez
*Assistant Examiner* — Lucas Palmer

(57) ABSTRACT

A surgical stapling device and method for joining tissue portions are provided including a handle assembly, an elongate body extending from the handle assembly, a cartridge assembly supported on a distal end of the elongate body, and an anvil assembly at a distal end of the surgical stapling device. The anvil assembly includes a shaft for removably coupling the anvil assembly to the cartridge assembly and a head pivotally mounted to a distal end of the shaft. A sleeve member is slidably disposed about the shaft of the anvil assembly and is transitionable between a first position, where the sleeve member engages the head of the anvil assembly to secure the head in an un-tilted condition, and a second position, where the sleeve member is disengaged from the head of the anvil assembly to allow the head to tilt.

8 Claims, 14 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant ............... A61B 17/115 227/179.1 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A * | 12/1996 | Schnut ............... A61B 17/115 227/175.1 |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A * | 4/2000 | Green ............... A61B 17/115 227/179.1 |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 * | 2/2001 | Bittner ............... A61B 17/1114 227/180.1 |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 * | 7/2001 | Balazs ............... A61B 17/115 227/175.1 |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |

(56) References Cited

U.S. PATENT DOCUMENTS

| | | | |
|---|---|---|---|
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 * | 8/2002 | Perry | A61B 17/072 227/175.2 |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 * | 1/2003 | Huxel | A61B 17/0643 227/179.1 |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,626,921 B2 | 9/2003 | Blatter et al. | |
| 6,629,630 B2 * | 10/2003 | Adams | A61B 1/00071 227/179.1 |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 * | 9/2005 | Gresham | A61B 17/115 227/175.1 |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B1 | 6/2007 | McGuckin, Jr. | |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |
| 7,455,682 B2 | 11/2008 | Viola | |
| 7,481,347 B2 | 1/2009 | Roy | |
| 7,494,038 B2 * | 2/2009 | Milliman | A61B 17/115 227/176.1 |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,556,186 B2 | 7/2009 | Milliman | |
| 7,559,451 B2 | 7/2009 | Sharma et al. | |
| 7,585,306 B2 | 9/2009 | Abbott et al. | |
| 7,588,174 B2 | 9/2009 | Holsten et al. | |
| 7,600,663 B2 | 10/2009 | Green | |
| 7,611,038 B2 | 11/2009 | Racenet et al. | |
| 7,635,385 B2 | 12/2009 | Milliman et al. | |
| 7,669,747 B2 | 3/2010 | Weisenburgh, II et al. | |
| 7,686,201 B2 | 3/2010 | Csiky | |
| 7,694,864 B2 | 4/2010 | Okada et al. | |
| 7,699,204 B2 | 4/2010 | Viola | |
| 7,708,181 B2 | 5/2010 | Cole et al. | |
| 7,717,313 B2 | 5/2010 | Criscuolo et al. | |
| 7,721,932 B2 | 5/2010 | Cole et al. | |
| 7,726,539 B2 | 6/2010 | Holsten et al. | |
| 7,743,958 B2 | 6/2010 | Orban, III | |
| 7,744,627 B2 | 6/2010 | Orban, III et al. | |
| 7,770,776 B2 | 8/2010 | Chen et al. | |
| 7,771,440 B2 | 8/2010 | Ortiz et al. | |
| 7,776,060 B2 | 8/2010 | Mooradian et al. | |
| 7,793,813 B2 | 9/2010 | Bettuchi | |
| 7,802,712 B2 | 9/2010 | Milliman et al. | |
| 7,823,592 B2 | 11/2010 | Bettuchi et al. | |
| 7,837,079 B2 | 11/2010 | Holsten et al. | |
| 7,837,080 B2 | 11/2010 | Schwemberger | |
| 7,837,081 B2 | 11/2010 | Holsten et al. | |
| 7,845,536 B2 | 12/2010 | Viola et al. | |
| 7,845,538 B2 | 12/2010 | Whitman | |
| 7,857,187 B2 | 12/2010 | Milliman | |
| 7,886,951 B2 | 2/2011 | Hessler | |
| 7,896,215 B2 | 3/2011 | Adams et al. | |
| 7,900,806 B2 | 3/2011 | Chen et al. | |
| 7,909,039 B2 | 3/2011 | Hur | |

(56) References Cited

U.S. PATENT DOCUMENTS

| | | | |
|---|---|---|---|
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2* | 9/2011 | Whitman | A61B 17/115 227/155 |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky et al. |
| 8,453,906 B2* | 6/2013 | Huang | A61B 17/07207 227/175.2 |
| 8,496,157 B2* | 7/2013 | Olson | A61B 17/1155 227/176.1 |
| 2002/0063143 A1* | 5/2002 | Adams | A61B 1/00087 227/180.1 |
| 2003/0111507 A1 | 6/2003 | Nunez |
| 2004/0195289 A1* | 10/2004 | Aranyi | A61B 17/072 227/180.1 |
| 2005/0051597 A1 | 3/2005 | Tolendano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1* | 1/2006 | Okada | A61B 17/1114 227/175.1 |
| 2006/0047307 A1 | 3/2006 | Ortiz et al. |
| 2006/0085033 A1* | 4/2006 | Criscuolo | A61B 17/00491 606/219 |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0023475 A1* | 2/2007 | Csiky | A61B 17/115 227/175.1 |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0075117 A1* | 4/2007 | Milliman | A61B 17/115 227/179.1 |
| 2009/0230170 A1* | 9/2009 | Milliman | A61B 17/0686 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1* | 4/2010 | Milliman | A61B 1/31 227/175.1 |
| 2010/0096435 A1* | 4/2010 | Fuchs | A61B 17/1114 227/179.1 |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1* | 7/2010 | Wenchell | A61B 17/115 227/176.1 |
| 2010/0200635 A1* | 8/2010 | Milliman | A61B 17/115 227/175.1 |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0237132 A1* | 9/2010 | Measamer | A61B 17/115 227/180.1 |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1* | 12/2010 | Milliman | A61B 17/1114 227/175.1 |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0152861 A1 | 6/2011 | Weisshaupt et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0012636 A1* | 1/2012 | Beckman | A61B 17/07207 227/175.1 |
| 2012/0273547 A1* | 11/2012 | Hodgkinson | A61B 17/07207 227/176.1 |
| 2013/0105544 A1* | 5/2013 | Mozdzierz | A61B 17/1155 227/175.1 |
| 2013/0181036 A1* | 7/2013 | Olson | A61B 17/1155 227/180.1 |
| 2013/0193191 A1* | 8/2013 | Stevenson | A61B 17/07292 227/179.1 |
| 2014/0131417 A1* | 5/2014 | Williams | A61B 17/068 227/175.3 |

(56) References Cited

U.S. PATENT DOCUMENTS

| | | | | |
|---|---|---|---|---|
| 2014/0144969 A1* | 5/2014 | Scheib | ............... | A61B 17/1155 227/175.1 |
| 2014/0367450 A1* | 12/2014 | Williams | ............. | A61B 17/115 227/181.1 |
| 2015/0069108 A1* | 3/2015 | Williams | ............ | A61B 17/1114 227/175.1 |

FOREIGN PATENT DOCUMENTS

| | | | |
|---|---|---|---|
| DE | 3301713 | A1 | 7/1984 |
| DE | 202010013152 | U1 | 3/2011 |
| EP | 0152382 | A2 | 8/1985 |
| EP | 0173451 | A1 | 3/1986 |
| EP | 0190022 | A2 | 8/1986 |
| EP | 0282157 | A1 | 9/1988 |
| EP | 0503689 | A2 | 9/1992 |
| EP | 1354560 | A2 | 10/2003 |
| FR | 1461464 | A | 2/1966 |
| FR | 1588250 | A | 4/1970 |
| FR | 2443239 | A1 | 7/1980 |
| GB | 1185292 | A | 3/1970 |
| GB | 2016991 | A | 9/1979 |
| GB | 2070499 | A | 9/1981 |
| NL | 7711347 | A | 4/1979 |
| SU | 1509052 | A1 | 9/1989 |
| WO | WO 8706448 | A | 11/1987 |
| WO | WO 8900406 | A1 | 1/1989 |
| WO | WO 9006085 | A1 | 6/1990 |
| WO | WO 2001/054594 | A1 | 8/2001 |
| WO | 03030745 | A1 | 4/2003 |
| WO | WO 2005037084 | A2 * | 4/2005 ........... A61B 17/068 |
| WO | WO 2008/107918 | A1 | 9/2008 |
| WO | 2012125615 | A2 | 9/2012 |
| WO | WO 2012125615 | A2 * | 9/2012 ......... A61B 17/1155 |

OTHER PUBLICATIONS

Australian Office Action dated Nov. 3, 2016, issued in Australian Application No. 2013206141.

European Search Report dated Mar. 24, 2017, issued in EP Application No. 16196108.

* cited by examiner

T-SLOT TILT ANVIL FOR CIRCULAR STAPLING INSTRUMENT

CROSS-REFERENCE TO RELATED APPLICATIONS

This application claims the benefit of and priority to U.S. Provisional Patent Application No. 61/668,540, filed Jul. 6, 2012, the entire disclosure of which is incorporated by reference herein.

BACKGROUND

Technical Filed

The present disclosure relates to surgical instrumentation for performing a surgical procedure. More particularly, the present disclosure relates to circular stapling instruments.

Background of Related Art

Circular staplers are known, as are their use in closed procedures, i.e., endoscopic, laparoscopic or through natural body orifices. Typically the circular staplers include a cartridge assembly on a distal end of an elongate body. The cartridge assembly includes a mechanism for forming staples and a knife for cutting the stapled tissue. Actuation of the cartridge assembly may be performed by a manually operated trigger or a powered drive assembly. Generally, both the actuation of the staple forming mechanism and the advancement of the knife occur at the same time, i.e., simultaneously.

Circular staplers which include an anvil assembly having a tilt-able anvil head are well known in the art. In some known circular staplers, tilting anvil mechanisms are spring loaded to tilt to a maximum angle allowed by the circular stapler and/or anvil geometry. Tilting the anvil head to its maximum angle facilitates pulling the anvil head through an anastomosis ring.

In some instances, however, it may be necessary to provide a tilt mechanism that can provide a greater tilting force than the biasing force generated by the spring loading to tilt the anvil head or maintain the anvil head in the tilted condition.

SUMMARY

Accordingly, it would be beneficial to have a surgical stapling device which includes a tilt mechanism that is capable of generating a greater tilting force than the biasing force of a spring. In accordance with an embodiment of the present disclosure, a surgical stapling device is provided which includes an anvil sleeve having an arm member for engaging the anvil head to tilt the anvil head when the anvil head is un-approximated after firing of the surgical stapling device.

In an aspect of the present disclosure, a surgical stapling device for joining tissue portions is provided. The surgical stapling device includes a handle assembly, an elongate body extending from the handle assembly, a cartridge assembly supported on a distal end of the elongate body, an anvil assembly at a distal end of the surgical stapling device, and an anvil sleeve including an elongate portion slidably disposed about the shaft of the anvil assembly and an arm extending from the elongate portion. The cartridge assembly includes a staple cartridge containing a plurality of surgical staples in an annular array. The anvil assembly has a shaft for removably coupling the anvil assembly to the cartridge assembly and a head pivotally mounted to a distal end of the shaft. The anvil assembly is translatable relative to the cartridge assembly between a first position, where the anvil assembly is spaced from the cartridge assembly, and a second position, where the anvil assembly is approximated relative to the cartridge assembly for clamping tissue disposed therebetween. The head of the anvil assembly is transitionable between a first condition, where a tissue contacting surface of the head is substantially perpendicular to the shaft, and a second condition, where the tissue contacting surface of the head is tilted relative to the shaft. The anvil sleeve is transitionable between a first position, where the elongate portion of the anvil sleeve is engaged to the head of the anvil assembly to secure the head in the first condition, and a second position, where the elongate portion of the anvil sleeve is spaced from head of the anvil assembly to allow the head to transition to the second condition. The arm is configured to engage the anvil head when the anvil sleeve transitions to the second position to transition the anvil head to the second condition.

In an aspect of the present disclosure, the elongate portion of the anvil sleeve includes at least one recess configured and dimensioned to receive a protrusion of the anvil head therein when the anvil sleeve is in the first position to inhibit transition of the anvil head from the first condition to the second condition.

In an aspect of the present disclosure, the arm extends through a channel in the anvil head and includes a flange disposed on an opposite side of the anvil head from the elongate portion. The flange is configured to engage the anvil head when the anvil sleeve transitions to the second position to transition the anvil head to the second condition.

In an aspect of the present disclosure, the arm includes at least one protrusion configured for releasable engagement with a recess of the anvil head to inhibit transitioning of the anvil sleeve relative to the anvil assembly from the first position to the second position.

In an aspect of the present disclosure, the cartridge assembly includes a locking sleeve. The locking sleeve is translatable relative to the anvil sleeve to engage the anvil sleeve when the anvil assembly is in the second position and is configured to disengage the anvil sleeve from the anvil assembly during transition of the anvil assembly from the second position to the first position.

In an aspect of the present disclosure, the locking sleeve is axially translatable relative to the cartridge assembly and includes a longitudinally extending slot configured for sliding reception of a tab of the cartridge assembly therein. The tab is configured to engage a proximal end of the slot to inhibit distal advancement of the locking sleeve relative to the cartridge assembly.

In an aspect of the present disclosure, the locking sleeve includes at least one tab configured for engagement with a lip of the elongate portion of the anvil sleeve to disengage the anvil sleeve from the anvil assembly during transition of the anvil assembly from the second position to the first position.

In an aspect of the present disclosure, the elongate portion includes a distal portion, a central portion and a proximal portion. The central portion is recessed relative to the distal and proximal portions such that the central portion and proximal portions define the lip at the interface therebetween.

In an aspect of the present disclosure, the at least one tab is biased inward toward the elongate portion of the anvil sleeve.

In an aspect of the present disclosure, each tab includes an arcuate portion extending from a distal end of the locking member, a longitudinal portion extending proximally from the arcuate portion, and a leg extending from the longitudinal portion through an opening of the locking sleeve.

In an aspect of the present disclosure, the at least one tab is disposed in a recess of the cartridge assembly when the locking sleeve is in a first, proximal position, and is configured to release from the recess of the cartridge assembly and engage the lip of the anvil sleeve when the locking sleeve is transitioned to at least one subsequent distal position.

In an aspect of the present disclosure, the cartridge assembly includes a knife pusher operably coupled to the handle assembly and configured to distally advance a knife blade to sever tissue disposed radially inward of the staple cartridge upon actuation of the handle assembly.

In an aspect of the present disclosure, the knife pusher includes at least one recess at a distal end thereof. The at least one recess is configured to engage a respective tab of the locking sleeve upon distal advancement of the knife pusher to advance the locking sleeve distally from the first, proximal position to the at least one subsequent distal position.

In an aspect of the present disclosure, the cartridge assembly further includes a staple pusher operatively associated with the handle assembly and configured to drive the staples out of the cartridge assembly upon actuation of the handle assembly.

In an aspect of the present disclosure, a surgical stapling device for joining tissue portions is disclosed. The surgical stapling device includes a handle assembly, an elongate body extending from the handle assembly, a cartridge assembly supported on a distal end of the elongate body, an anvil assembly at a distal end of the surgical stapling device, and an anvil sleeve. The anvil sleeve includes an elongate portion slidably disposed about the shaft of the anvil assembly and an arm extending from the elongate portion. The cartridge assembly includes a staple cartridge containing a plurality of surgical staples in an annular array, a staple pusher configured for advancement through the staple cartridge to eject the plurality of surgical staples from the staple cartridge, a knife assembly configured for advancement through the cartridge assembly to sever tissue, and a drive member disposed within the cartridge assembly and in operative association with the handle assembly. The drive member configured to advance the staple pusher and the knife assembly upon actuation of the handle assembly. The anvil assembly has a shaft for removably coupling the anvil assembly to the cartridge assembly and a head pivotally mounted to a distal end of the shaft. The anvil assembly is translatable relative to the cartridge assembly between a first position, where the anvil assembly is spaced from the cartridge assembly, and a second position, where the anvil assembly is approximated relative to the cartridge assembly for clamping tissue disposed therebetween. The head of the anvil assembly is transitionable between a first condition, where a tissue contacting surface of the head is substantially perpendicular to the shaft, and a second condition, where the tissue contacting surface of the head is tilted relative to the shaft. The anvil sleeve is transitionable between a first position, where the elongate portion of the anvil sleeve is engaged to the head of the anvil assembly to secure the head in the first condition, and a second position, where the elongate portion of the anvil sleeve is spaced from head of the anvil assembly to allow the head to transition to the second condition. The arm is configured to engage the anvil head when the anvil sleeve transitions to the second position to transition the anvil head to the second condition.

In an aspect of the present disclosure, a method of use for a surgical stapling device having an anvil assembly with a pivoting head is disclosed. The method includes the steps of inserting the surgical stapling device into an opening in a body, positioning the surgical stapling device within the body such that a portion of tissue is disposed between an anvil assembly and a cartridge assembly of the surgical stapling device, translating the anvil assembly from a first position, where the anvil assembly is spaced from the cartridge assembly, to a second position, where the anvil assembly approximated relative to the cartridge assembly to clamp the tissue therebetween, translating a staple pusher relative to the cartridge assembly to urge a plurality of fasteners disposed in the cartridge assembly through the tissue towards the anvil assembly, translating a locking sleeve of the cartridge assembly relative to an anvil sleeve of the anvil assembly such that a portion of the locking sleeve engages the anvil sleeve, translating the anvil assembly from the second position to the first position where the anvil sleeve of the anvil assembly disengages from the anvil assembly due to the engagement of the locking sleeve with the anvil sleeve to allow the head to pivot, engaging an arm of the anvil sleeve against the head of the anvil assembly to pivot the head of the anvil assembly, and withdrawing the surgical stapling device from the body.

In an aspect of the present disclosure, translating the locking sleeve relative to the anvil sleeve includes translating a knife pusher of the cartridge assembly relative to the locking sleeve to engage the locking sleeve and translate the locking sleeve relative to the anvil sleeve.

In an aspect of the present disclosure, disengaging the anvil sleeve from the anvil assembly includes disengaging a protrusion of the anvil head from a recess of the anvil sleeve.

In an aspect of the present disclosure, engaging the locking sleeve with the anvil sleeve includes engaging a leg of the locking sleeve against a lip of the anvil sleeve.

In an aspect of the present disclosure, disengaging the anvil sleeve from the anvil assembly includes spacing apart an elongate portion of the anvil sleeve from the head of the anvil assembly.

Any of the above aspects of the present disclosure described may be combined with any other aspect of the present disclosure without departing from the scope of the present disclosure.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Embodiments of the presently disclosed circular stapling instrument including a tilt-able anvil head will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
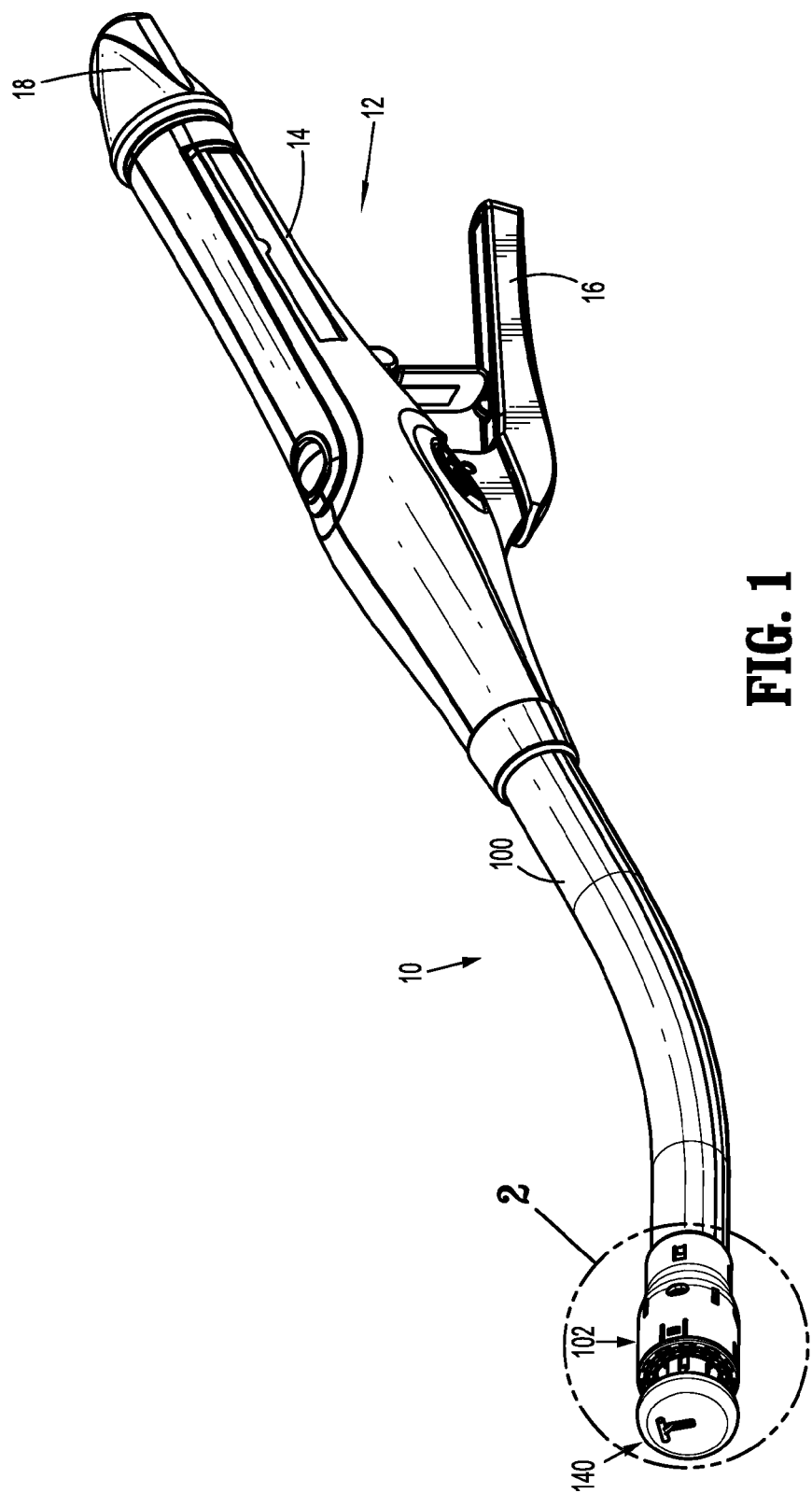
FIG. 1 is a perspective view of an exemplary circular stapler according to the present disclosure.
Figure 2:
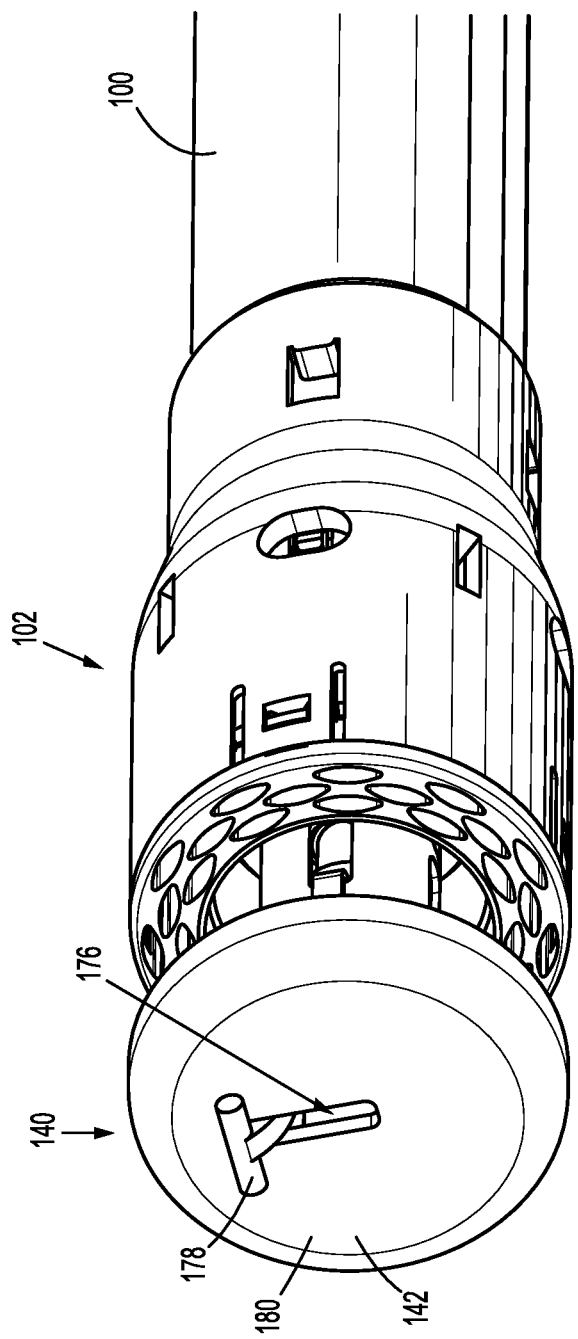
FIG. 2 is a perspective view of the area of detail from FIG. 1, illustrating a tool assembly of the circular stapler of FIG. 1.
Figure 3:
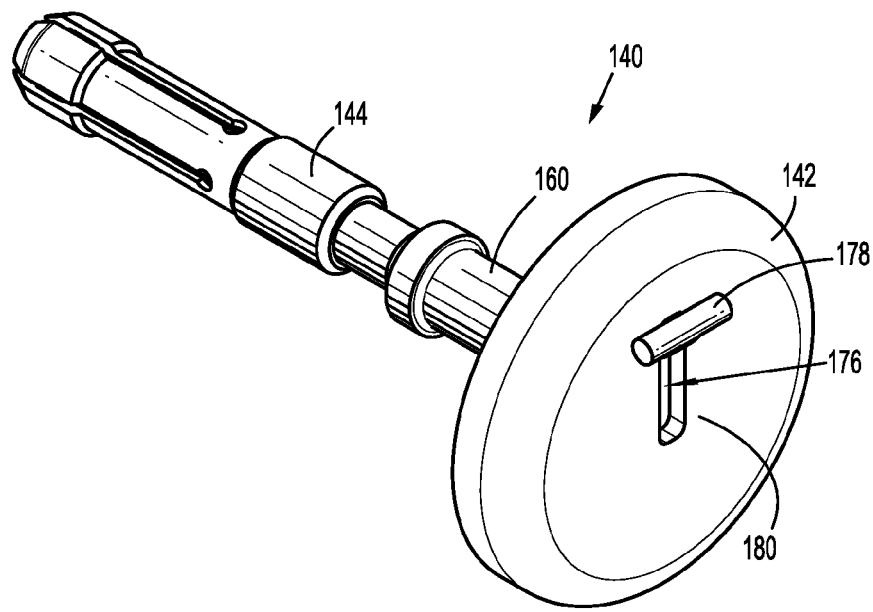
FIG. 3 is a perspective view of an anvil assembly of the tool assembly of FIG. 2.

Referring initially to FIG. 1, a circular stapler is disclosed herein and is generally designated as circular stapler 10. Circular stapler 10 includes a handle assembly 12 and an elongate body 100 coupled to a distal end of handle assembly 12. A cartridge assembly 102 is mounted on a distal end of elongate body 100.

Handle assembly 12 includes a fixed handle 14 and a moveable handle or trigger 16. Handle assembly 12 also includes an adjustment knob 18 for moving anvil assembly 140 relative to cartridge assembly 102. The structure and function of handle assembly 12 will only be described herein to the extent necessary to fully disclose the operation of cartridge assembly 102. Examples of instruments for performing circular anastomosis of hollow organs are described in U.S. Pat. Nos. 6,053,390; 5,588,579; 5,119,987; 5,005,749; 4,646,745; 4,576,167; and 4,473,077, each of which is incorporated herein in its entirety by reference.

Elongate body 100 may extend from handle assembly 12 or may be removably attached to handle assembly 12 and may be constructed so as to have a curved shape along its length. It is contemplated that elongate body 100 may be substantially rigid or may be flexible without departing from the scope of the present disclosure.

Handle assembly 12 may include a powered actuation mechanism configured to supply linear motion through elongate body 100 to cartridge assembly 102. For example, handle assembly 12 may include an electric motor or other electrical device (not shown) which produces rotational motion upon actuation of trigger 16 and converts the rotational motion into linear motion which is transmitted through elongate body 100 via a drive assembly (not shown) for use by cartridge assembly 102. It is contemplated that the motor or other electrical device may instead produce linear motion directly. Examples of instruments including powered actuation mechanisms for use with surgical stapling devices are described in co-pending U.S. patent application Ser. No. 12/946,082 entitled "ADAPTERS FOR USE BETWEEN SURGICAL HANDLE ASSEMBLY AND SURGICAL END EFFECTOR" which is incorporated herein in its entirety by reference.

Figure 10:
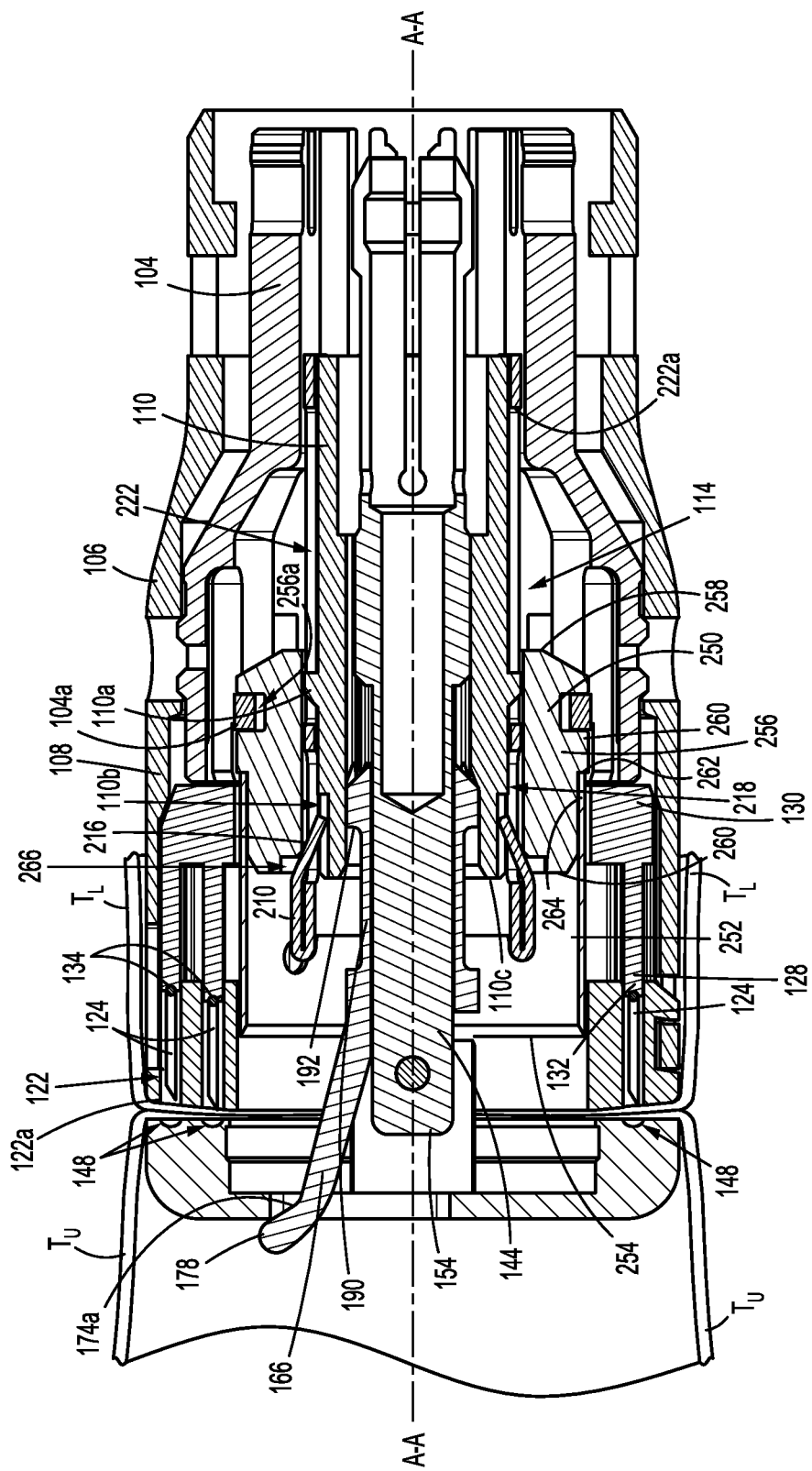
FIG. 10 is a side, cross-sectional view of the tool assembly of FIG. 2, illustrating tissue clamped between the anvil assembly and the cartridge assembly prior to firing of the circular stapler.

Cartridge assembly 102 defines a longitudinal axis A-A (FIG. 10). In one embodiment, cartridge assembly 102 is removably secured to elongate body 100 such that cartridge assembly 102 may be replaced and the circular stapler 10 may be reused. Alternatively, circular stapler 10 is configured for a single use, i.e., disposable.

Circular stapler 10 (FIG. 1) also includes an anvil assembly 140 positioned distally of cartridge assembly 102 and removably insertable into cartridge assembly 102. Anvil assembly 140 is translatable along longitudinal axis A-A (FIG. 10) relative to cartridge assembly 102.

With reference now to FIGS. 2-5, anvil assembly 140 includes an anvil head 142 and an anvil shaft 144. Anvil shaft 144 is insertable into an inner bore 116 (FIG. 9) of cartridge assembly 102 and is removably and slidably securable within inner bore 116 of cartridge assembly 102. Shaft 144 is configured to be actuatable by handle assembly 12 (FIG. 1) to translate anvil assembly 140 axially along longitudinal axis A-A (FIG. 10) relative to cartridge assembly 102 to approximate or un-approximate anvil assembly 140 relative to cartridge assembly 102. For example, adjustment knob 18 (FIG. 1) may be actuated to translate anvil assembly 140 relative to cartridge assembly 102 to adjust the spacing between anvil head 142 and cartridge assembly 102 and trigger 16 (FIG. 1) may be actuated to approximate anvil head 142 relative to cartridge assembly 102 to grasp tissue disposed therebetween.

Anvil head 142 includes a tissue contacting surface 146 (FIG. 5) defining staple forming pockets 148 (FIG. 10). In an initial un-tilted condition (FIG. 10), tissue contacting surface 146 is configured to be substantially perpendicular to longitudinal axis A-A. Anvil head 142 is coupled to anvil shaft 144 by a pivot assembly 150 and is rotatable about pivot assembly 150 to tilt anvil head 142 to a final tilted condition (FIGS. 16 and 17) such that tissue contacting surface 146 is approximately aligned with or slightly offset relative to longitudinal axis A-A. For example, one portion of tissue contacting surface 146 may define an acute angle with longitudinal axis A-A while a remaining portion of tissue contacting surface 146 on an opposite side of shaft 144 may define an obtuse angle with longitudinal axis A-A.

Pivot assembly 150 includes an anvil base 152 of anvil head 142 and a distal end 154 (FIG. 10) of shaft 144. Distal end 154 of shaft 144 is inserted into anvil base 152 and rotatably secured therein by a pin 156. Anvil base 152 includes a slot 158 extending radially therethrough to allow anvil head 142 to tilt or pivot. For example, when the anvil head 142 pivots from the initial un-tilted condition to the final tilted condition (FIG. 17), slot 158 of anvil base 152 receives at least a portion of the distal end 154 of shaft 144 therein.

Figure 4:
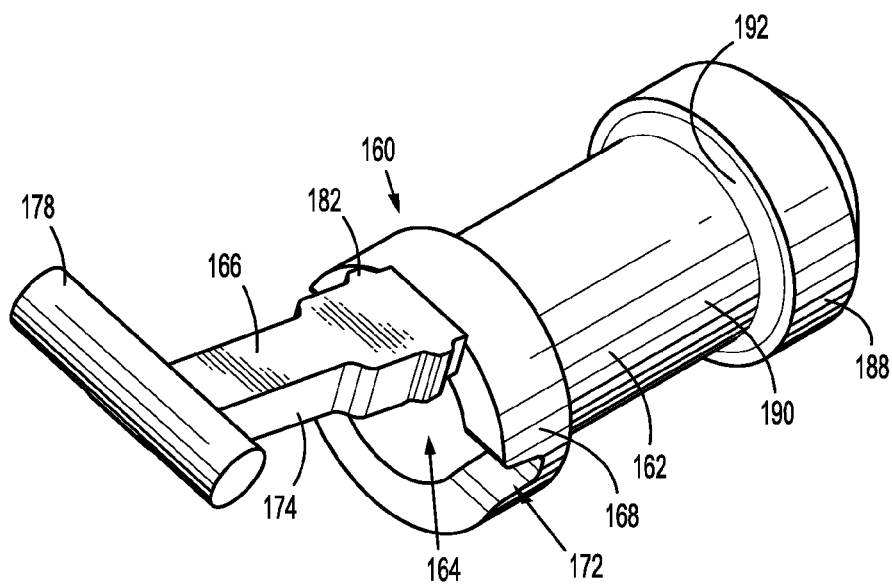
FIG. 4 is a perspective view of an anvil sleeve of the anvil assembly of FIG. 3.
Figure 5:
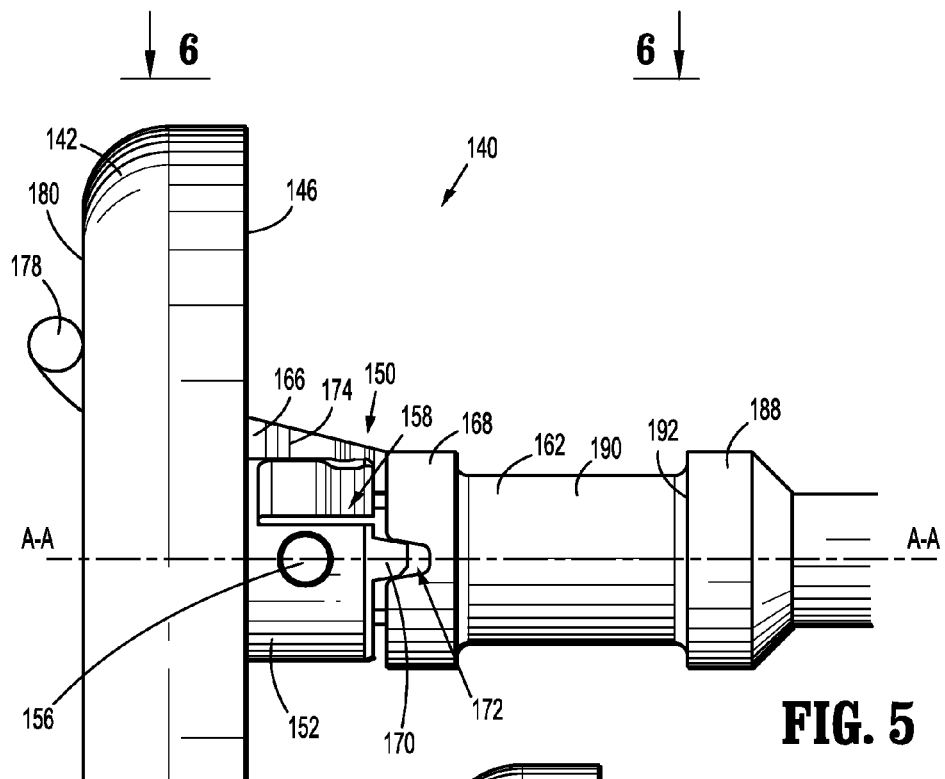
FIGS. 5 is a side, plan view of the anvil assembly of FIG. 3.
Figure 6:
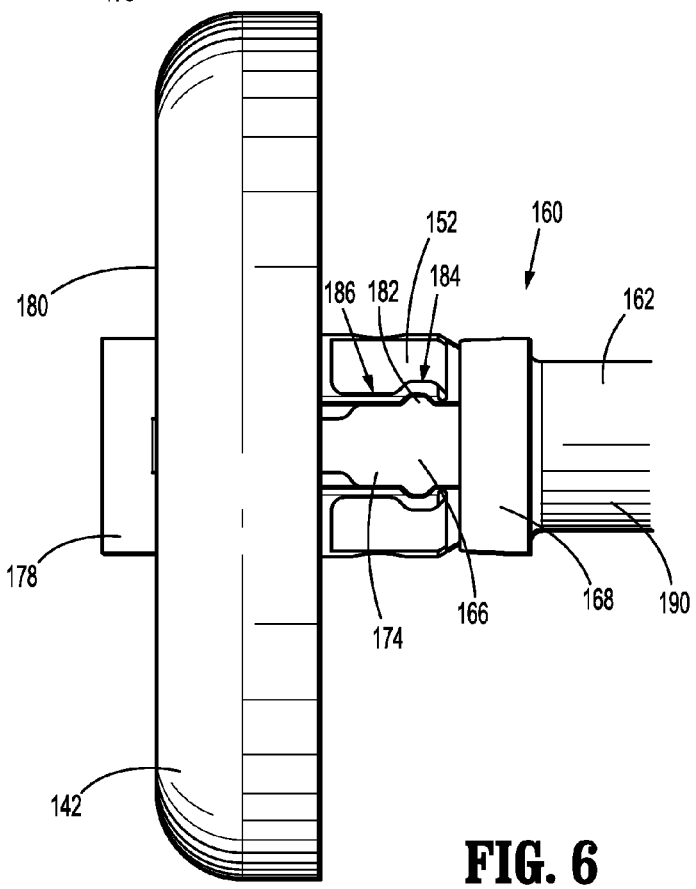
FIGS. 6 is a side, plan view of the anvil assembly of FIG. 5, taken along 6-6.
Figure 7:
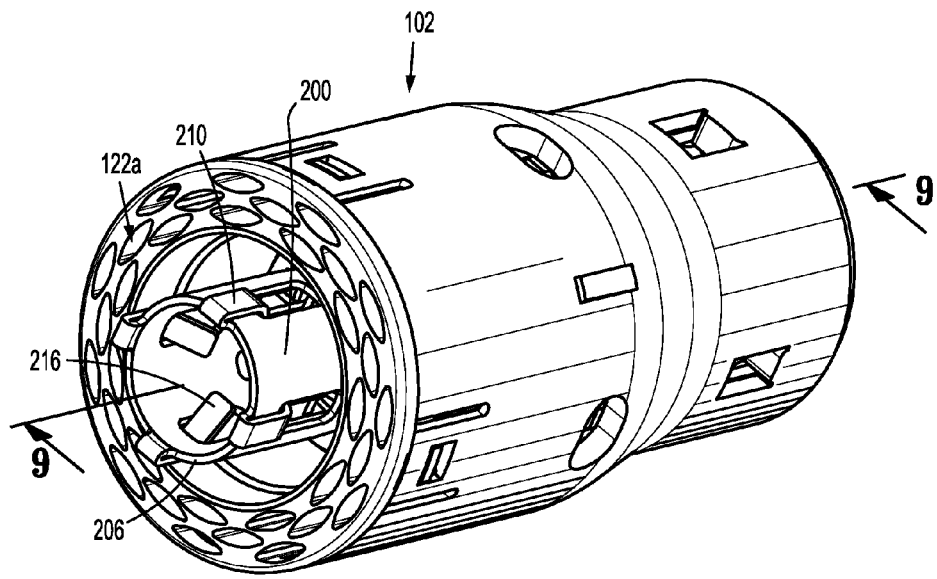
FIG. 7 is a perspective view of a cartridge assembly of the tool assembly of FIG. 2.
Figure 8:
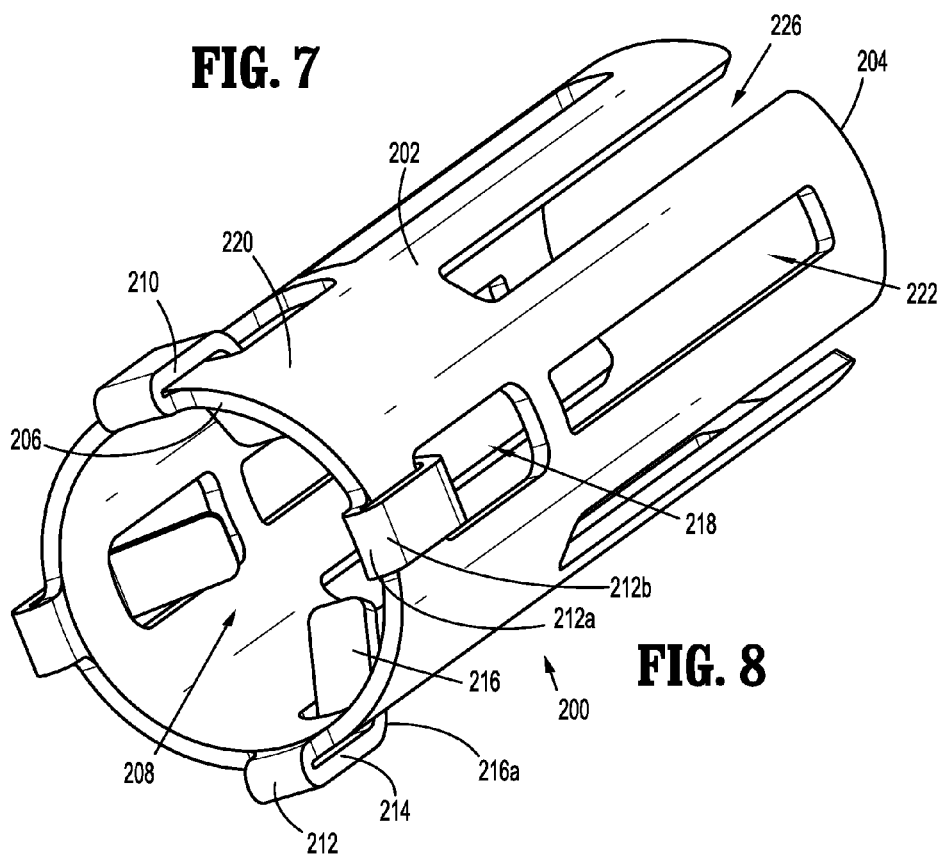
FIG. 8 is a perspective view of a locking sleeve of the cartridge assembly of FIG. 7.

Referring now to FIGS. 4-6, anvil assembly 140 also includes an anvil sleeve 160 coaxially mounted about anvil shaft 144 and axially translatable along longitudinal axis A-A relative to anvil head 142 and shaft 144. Anvil sleeve 160 includes an elongate portion 162 including a central lumen 164 extending therethrough for the reception of shaft 144. Elongate portion 162 has a distal portion 168, proximal portion 188 and central portion 190. Distal portion 168 includes an arm 166 extending therefrom and a recess 172 dimensioned to receive a protrusion 170 extending from anvil base 152 therein when anvil sleeve 160 is in a first position. Engagement between the protrusion 170 and the recess 172 inhibits tilting of anvil head 142. It is contemplated that elongate portion 162 of sleeve 160 may include more than one recess 172 each dimensioned to receive a proximally extending protrusion 170 of anvil base 152. Central portion 190 is recessed relative to distal portion 168 and proximal portion 188 such that a lip 192 is defined by the interface between proximal portion 188 and central portion 190.

Arm 166 includes a base portion 174 extending through a channel 176 (FIG. 3) of anvil head 142 and a flange 178 disposed at a distal end portion of the base portion 174. Flange 178 is disposed on an opposite side of the channel 176 relative to elongate portion 162. Base portion 174 may define an arcuate portion 174a (FIG. 10) adjacent flange 178 such that arm member flares outward relative to the longitudinal axis A-A. Channel 176 extends radially along and longitudinally through anvil head 142. Flange 178 of arm 166 is configured to engage a top surface 180 of anvil head 142 during movement of anvil sleeve 160 relative to anvil head 142 between a first position, where elongate portion 162 of anvil sleeve 160 is engaged with anvil base 152 of anvil head 142, and a second position, where elongate portion 162 is spaced relative to anvil base 152, such that flange 178 transitions the anvil head 142 from the initial un-tilted condition to the final tilted condition. For example, flange 178 may be substantially perpendicular to the longitudinal axis A-A and may be a rounded or cylindrical in shape to assist in sliding along channel 176 of anvil head 142. It is contemplated that flange 178 may have any other shapes suitable for engaging top surface 180 of anvil head 142 including, for example, a cube, sphere, cuboid, hexagonal prism, etc. Base portion 174 and flange 178 of arm 166 may together define a substantially T-shape. The use of flange 178 to effect tilting of anvil head 142 provides substantial benefits over the classic spring tilt anvil head design. For example, by using flange 178 in conjunction with the un-approximation of anvil assembly 140, direct mechanical force, e.g. the use of knob 18, is utilized to tilt anvil head 142 instead of reliance on the innate bias of a spring member disposed in between the anvil base 152 and the anvil shaft 144. This provides a more reliable and efficient method of tilting anvil head 142.

Figure 13:
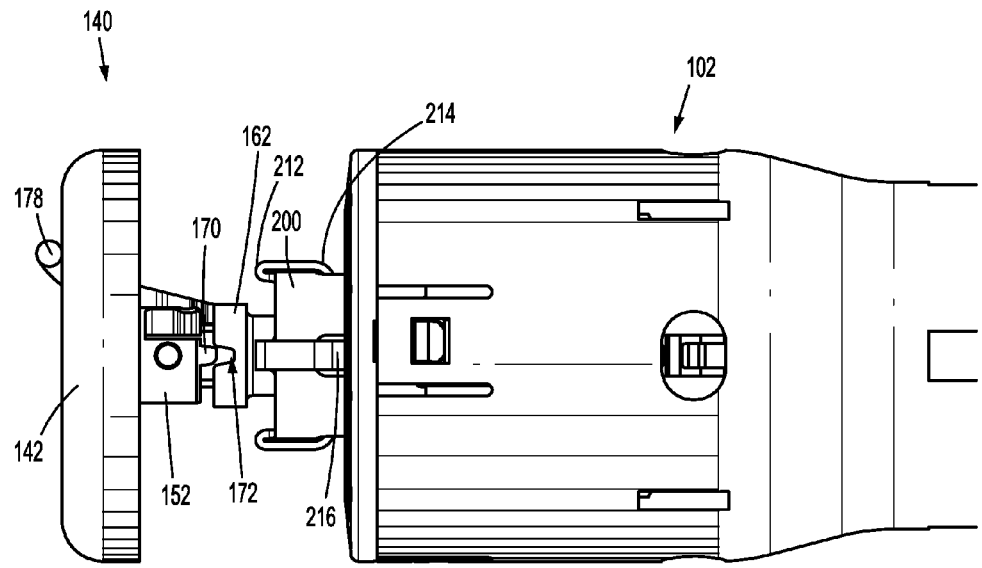
FIGS. 13 and 14 are side, plan views of the tool assembly of FIG. 12 after firing of the circular stapler, illustrating the anvil head being released from the anvil sleeve to allow the anvil head to tilt.
Figure 14:
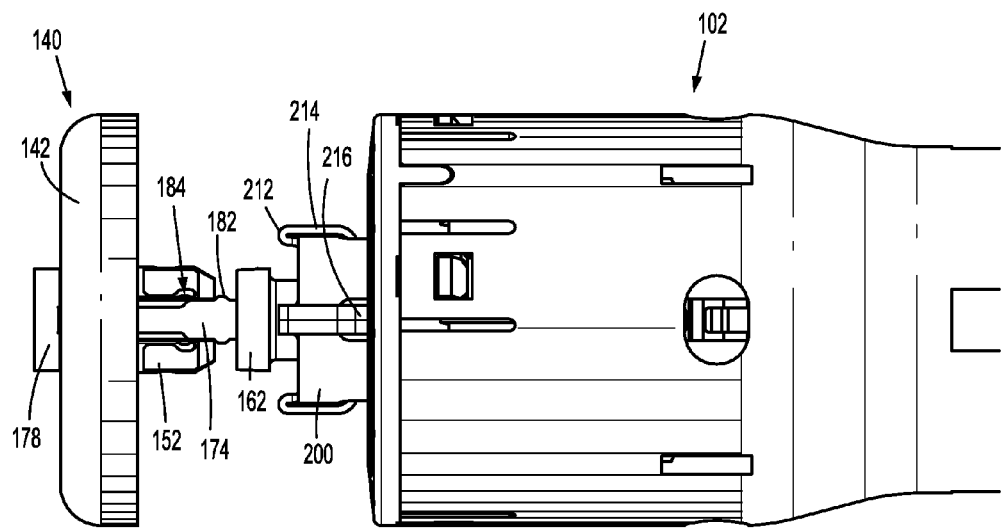

Referring now to FIGS. 13 and 14, during use, as anvil sleeve 160 translates relative to anvil head 142 toward the second position, elongate portion 162 is spaced apart from anvil base 152 to release protrusions 170 of anvil base 152 from the recesses 172 of elongate portion 162. Once protrusions 170 are released from recesses 172, anvil head 142 is free to tilt. As elongate portion 162 is spaced apart from anvil base 152, arm 166 is also translated relative to anvil head 142 such that arm member 174 engages top surface 180 of anvil head 142 to transition anvil head 142 from the un-tilted condition to the tilted condition. In this manner, tilting of anvil head 142 is achieved.

Referring now to FIGS. 6 and 14, base portion 174 of arm 166 includes a protrusion 182 configured for releasable engagement with a recess 184 in an inner surface 186 of anvil base 152 to releasably maintain anvil sleeve 160 in the first position relative to anvil head 142. It is contemplated that more than one protrusion 182 and more than one recess 184 may be provided.

Figure 9:
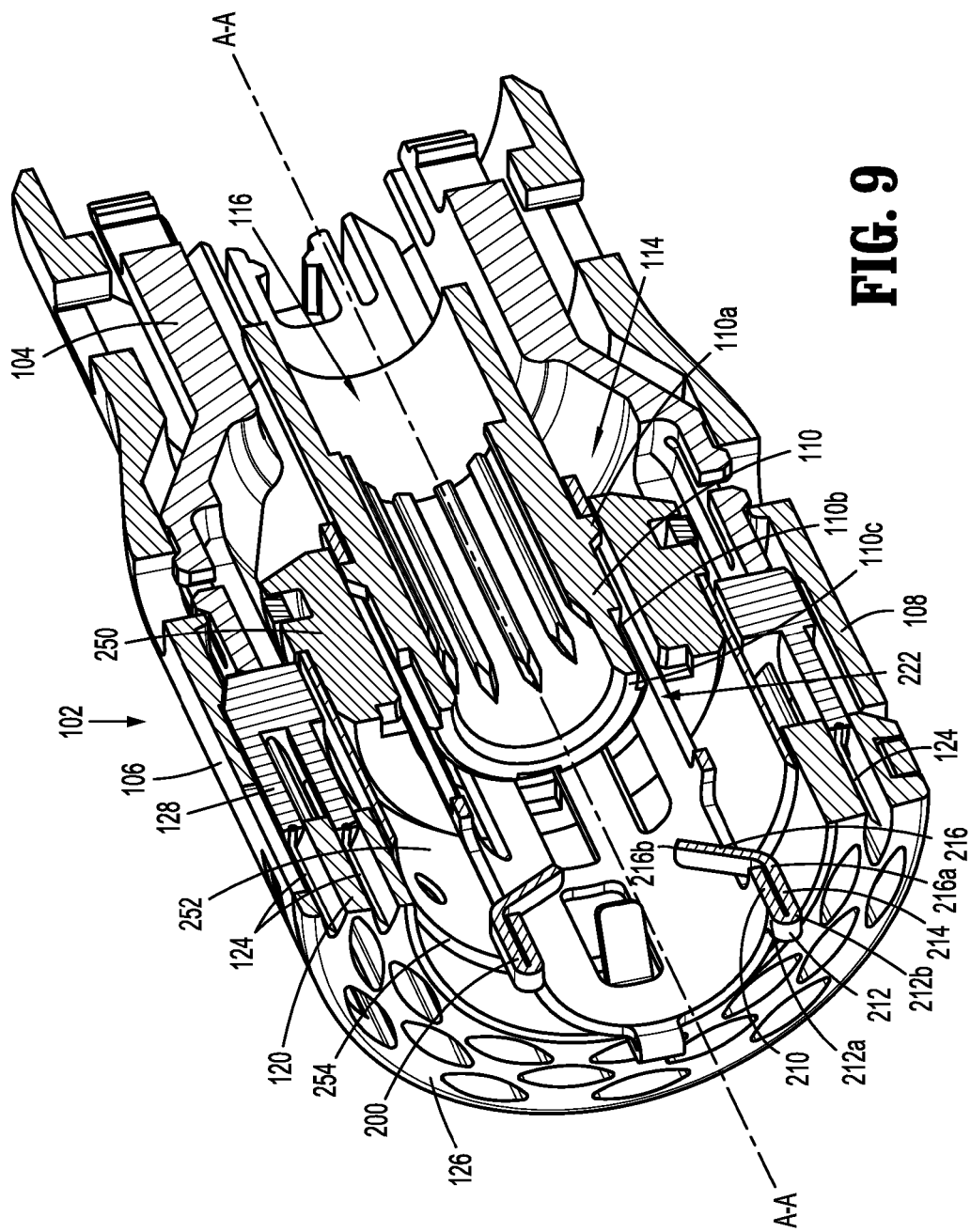
FIG. 9 is a cross-sectional view of the cartridge assembly of FIG. 7, taken along section line 9-9 of FIG. 7.
Figure 9A:
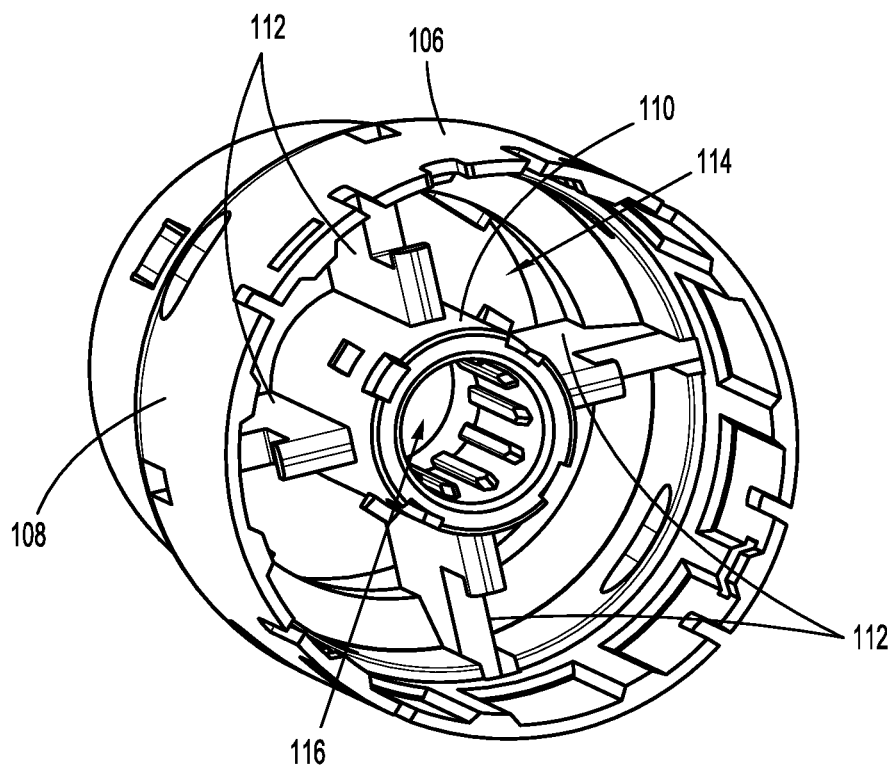
FIG. 9A is a perspective, end view of a housing of the cartridge assembly of FIG. 7.

With reference now to FIGS. 9, 9A, and 10, cartridge assembly 102 includes a drive member 104, a housing 106, a staple cartridge 120, a staple pusher 128, a knife assembly 250, and a locking sleeve 200. Staple cartridge 120 is operably mounted at a distal end of cartridge assembly 102 and, in one embodiment, staple cartridge 120 is removably secured to cartridge assembly 102 such that staple cartridge 120 may be replaced.

Housing 106 of cartridge assembly 102 includes an outer cylindrical portion 108, an inner cylindrical portion 110 and a plurality of radially extending supports or ribs 112 (FIG. 9A) extending between inner cylindrical portion 110 and outer cylindrical portion 108 Inner cylindrical portion 110 and outer cylindrical portion 108 of housing 106 are coaxial and define an annular channel 114 therebetween configured to receive staple pusher 128 and knife assembly 250. An inner bore 116 of cartridge assembly 102 extends through inner cylindrical portion 110 and is configured to receive shaft 144 of anvil assembly 140 therein for operable connection to adjustment knob 18 (FIG. 1).

Referring now to FIGS. 7-10, locking sleeve 200 includes a substantially cylindrical housing 202 having a proximal end 204 and a distal end 206 and defining an inner bore 208 therethrough for the reception of inner cylindrical portion 110 of housing 106. A plurality of tabs 210 extend from distal end 206 of housing 202. Each tab includes an arcuate portion 212, a longitudinal portion 214 extending from the arcuate portion 212, and a leg 216 extending from the longitudinal portion 214. Arcuate portion 212 extends distally from housing 202 at a first end 212a and wraps around, e.g. curls radially outward from housing 202, such that a second end 212b is oriented in a substantially proximal direction adjacent or proximate to housing 202. Longitudinal portion 214 extends proximally from second end 212b substantially parallel with cylindrical housing 202 to a first end 216a of leg 216. Each leg 216 extends through an opening 218 in a distal portion 220 of cylindrical housing 202 and into inner bore 208. Legs 216 may be biased toward inner bore 208. For example, there may be four tabs 210 extending from distal end 206 of housing 202 with legs 216 extending through four respective openings 218 of cylindrical housing 202.

Locking sleeve 200 also includes a plurality of longitudinally extending slots 222 extending through a distal portion 224 of cylindrical housing 202. Each slot 222 is configured for sliding reception of a tab 110a of inner cylindrical portion 110 of inner housing 106. Each tab 110a of inner cylindrical portion 110 and corresponding slot 222 of locking sleeve 200 allows locking sleeve 200 to slide relative to housing 106 between a first, proximal position, where a second end 216b of each leg 216 is disposed in a recess 110b extending proximally along inner cylindrical portion 110 from distal end 110c, and a second, distal position, where each leg 216 is distal of the respective recess 110b and snaps into or engages central portion 190 and/or lip 192 of anvil sleeve 160 to inhibit distal advancement of anvil sleeve 160 relative to distal end 110c of inner cylindrical portion 110 after firing of the surgical stapling device 10 when anvil assembly 140 is un-approximated relative to staple cartridge 120. It is contemplated that anvil sleeve 160 may at least partially advance distally relative to inner cylindrical portion 110 during un-approximation of anvil assembly 140 relative to staple cartridge 120 until tabs 110a engage the proximal ends 222a of their respective slots 222. Locking sleeve 200 also includes a plurality of slots 226 (FIG. 8) extending longitudinally from proximal end 204 and configured for sliding reception of supports 112 of housing 106 therethrough.

With reference now to FIGS. 9 and 10, staple cartridge 120 includes at least one annular array of staple receiving slots 122 disposed at a distal end and a staple 124 disposed in each of staple receiving slots 122. For example, staple cartridge 120 may include one, two, or more than two annular arrays of staple receiving slots 122. Staple receiving slots 122 include openings 122a extending through a tissue contacting surface 126 of the distal end of the staple cartridge 120. Staple cartridge 120 may be fixedly connected to the distal end of cartridge assembly 102 or may be configured to concentrically fit within the distal end of cartridge assembly 102.

Staple pusher 128 defines a substantially cylindrical shape and has a proximal portion 130 and a distal portion 132. Staple pusher 128 is coaxially and slidably disposed within channel 114, between outer cylindrical portion 108 and inner cylindrical portion 110. Distal portion 132 of staple pusher 128 defines a plurality of peripherally spaced fingers 134 in two concentric rows for engaging staples 124 within staple receiving slots 122. It is contemplated that one, two or more rows of fingers 134 may be included to correspond to the number of annular arrays of staple receiving slots 122 of staple cartridge 120. Each finger 134 of staple pusher 128 is received within one of the respective staple receiving slots 122 of staple cartridge 120 and is configured to translate through its respective staple receiving slot 122 and opening 122a during advancement of staple pusher 128 relative to cartridge assembly 102 to engage, drive and eject a respective staple 124 out of the opening 122a of the respective staple receiving slot 122, through tissue, and against a staple forming pocket 148 of anvil assembly 140 to thereby form staple 124. For example, staples 124 may be formed in a substantially B-shape.

Figure 11:
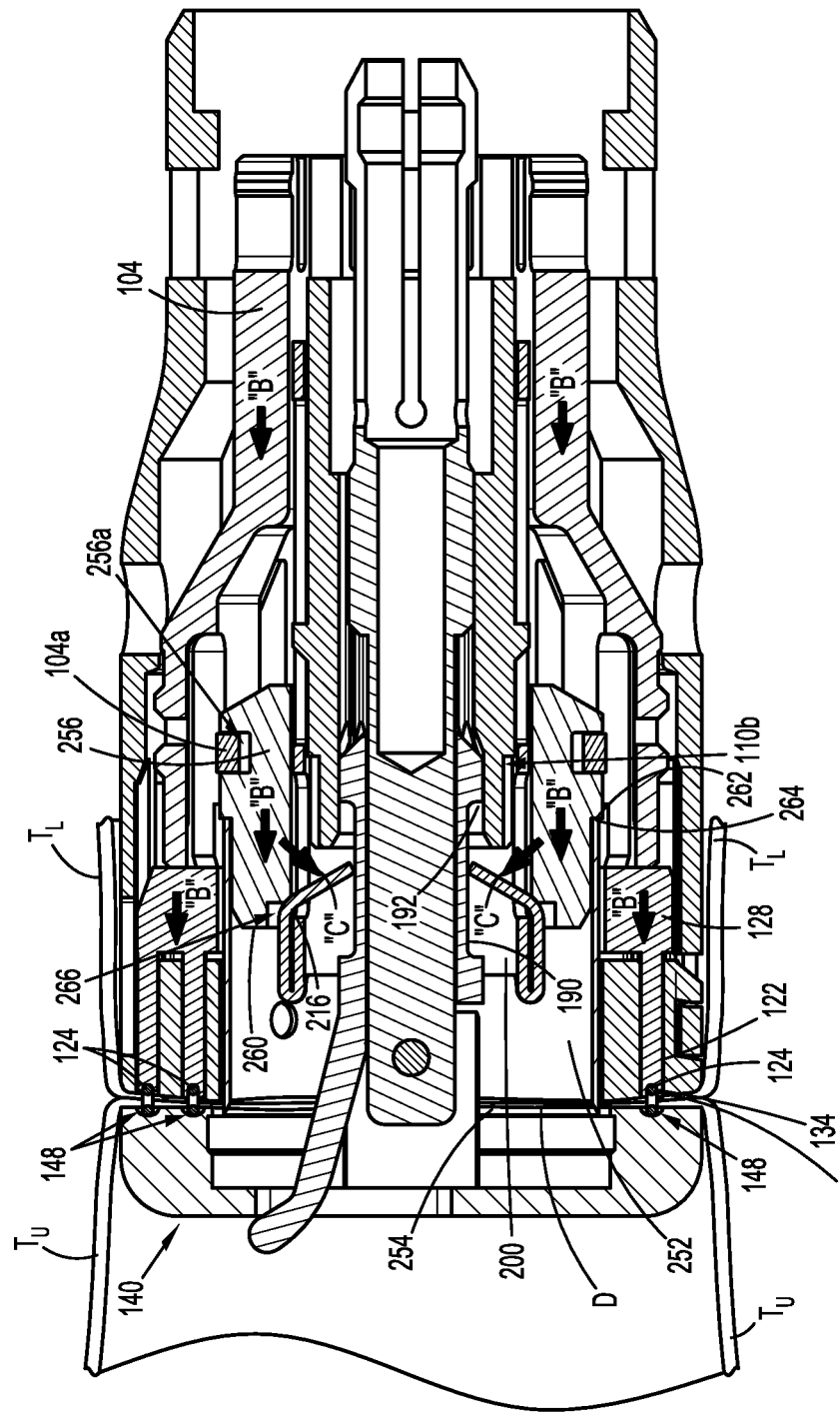
FIG. 11 is a side, cross-sectional view of the tool assembly of FIG. 10, illustrating the drive member, staple pusher and knife pusher being advanced in the direction "B" during firing.
Figure 12:
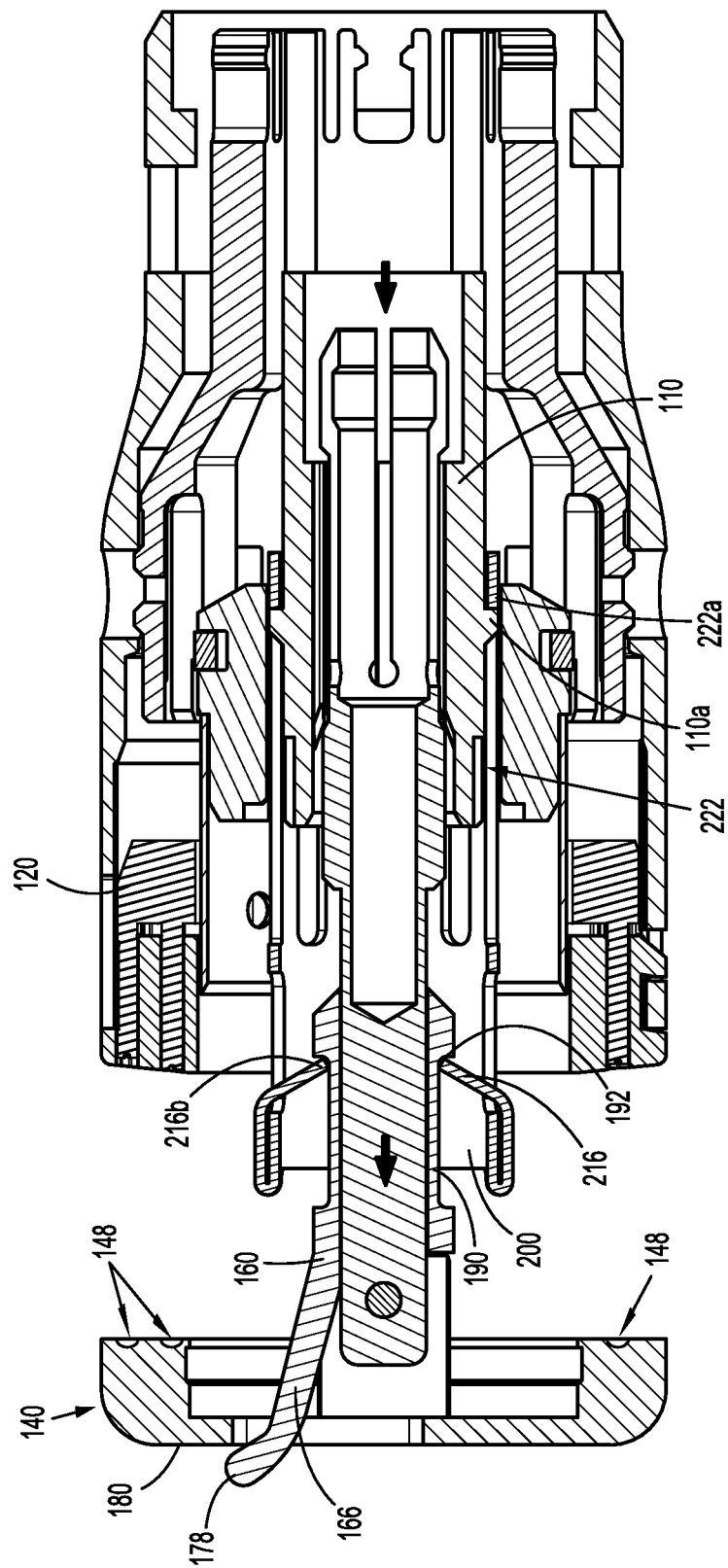
FIG. 12 is a side, cross-sectional view of the tool assembly of FIG. 11A, illustrating the anvil assembly being un-approximated relative to the cartridge assembly.

With reference to FIGS. 10-12, drive member 104 is slidably received within channel 114 of cartridge assembly 102 and is axially translatable within cartridge assembly 102 in response to actuation of trigger 16 (FIG. 1) of handle assembly 12 (FIG. 1). Drive member 104 is configured to engage a proximal portion or surface of staple pusher 128 during axial translation, e.g. distal advancement, to advance staple pusher 128 axially through cartridge assembly 102 and staple receiving slots 122. Advancement of staple pusher 128 through staple receiving slots 122 urges staples 124 out of staple receiving slots 122 through openings 122a. Drive member 104 may alternatively be coupled to staple pusher 128 by, for example, snap fit, friction fit, or other similar methods of coupling. Drive member 104 and staple pusher 128 may alternatively be monolithically formed. In an embodiment, staple pusher 128 remains in a substantially advanced position after firing when drive member 104 is axially translated back, e.g., translated proximally, to an initial pre-fired position.

With reference now to FIGS. 10-12, cartridge assembly 102 includes a knife assembly 250 slidably disposed in channel 114, radially inward of staple cartridge 120 and coaxially disposed about inner cylindrical portion 110 of housing 106. Knife assembly 250 is axially translatable along longitudinal axis A-A to sever a portion of the tissue disposed radially inward of staple cartridge 120 during actuation of circular stapler 10. Knife assembly 250 includes a knife blade 252 substantially in the form of an open cup or cylinder with the distal end thereof defining a knife edge 254.

As seen in FIGS. 6-10, knife assembly 250 includes a knife pusher 256 having a proximal end surface 258 and a distal end surface 260. Knife pusher 256 is operatively coupled to drive member 104 by a tab 104a of drive member 104 disposed within with a slot 256a of knife pusher 256 such that distal or proximal advancement of drive member 104 causes distal or proximal advancement of knife pusher 256 along longitudinal axis A-A. Drive member 104 may be coupled to knife pusher 256 by, for example, snap fit, friction fit, or other similar methods of coupling. Drive member 104 and knife pusher 256 may alternatively be monolithically formed.

Knife pusher 256 includes a flanged portion 260 extending radially therefrom and defining a lip 262 thereon that is configured for engagement with a proximal end 264 of knife blade 252 during distal advancement of knife pusher 256. Knife pusher 256 may be coupled to knife blade 252 by a snap fit, friction fit, or other similar methods of coupling. Knife blade 252 and knife pusher 256 may alternatively be monolithically formed.

Knife pusher 256 includes at least one recess 266 in distal end surface 260 for engagement with legs 216 of locking sleeve 200 during distal advancement of knife pusher 256 to urge locking sleeve 200 distally. The at least one recess 266 of knife pusher 256 drives legs 216 of locking sleeve 200 distally out of recesses 110b of inner housing 110 to allow legs 216 to bias inward through openings 208 to engage central portion 190 and/or lip 192 of anvil sleeve 160.

The operation of circular stapler 10 will now be described with reference to FIGS. 10-17. Referring initially to FIG. 10, cartridge assembly 102 is shown in an initial, or pre-fired condition, following approximation of anvil assembly 140 relative to cartridge assembly 102, with tissue "$T_U$" and "$T_L$" to be anastomosed disposed therebetween. In the initial condition, drive member 104, staple pusher 128, knife pusher 256 are disposed in initial proximal positions with the legs 216 of locking sleeve 200 disposed in the recesses 110b of inner cylindrical portion 110.

Prior to firing, shaft 144 and sliding sleeve 158 of anvil assembly 140 are inserted through an upper portion of tissue "$T_U$", staple cartridge 120 is positioned against a lower portion of tissue "$T_L$" and shaft 144 is inserted through lower portion of tissue "$T_L$" into inner bore 116 of cartridge assembly 102. Anvil assembly 140 is then approximated relative to staple cartridge 120 through actuation of knob 18 (FIG. 1) of handle assembly 12 (FIG. 1) to grasp or clamp the upper and lower portions of tissue "$T_U$" and "$T_L$" disposed therebetween. When anvil assembly 140 and staple cartridge 120 are approximated, at least a portion of anvil sleeve 160 is positioned within inner bore 116 of housing 106, through the lower portion of tissue "$T_L$." For clarity, upper and lower portions of tissue "$T_U$" and "$T_L$" will only be illustrated in the figures where necessary.

With reference now to FIG. 11, during the firing of circular stapler 10 (FIG. 1), following approximation of anvil assembly 140 against staple cartridge 120, retraction or actuation of trigger 16 (FIG. 1) relative to handle 14 (FIG. 1) causes advancement of a drive assembly (not shown) which operably engages drive member 104 to cause advancement of drive member 104 in the direction indicated by arrows "B". As drive member 104 advances, drive member 104 engages and drives staple pusher 128 in the direction indicated by arrows "B". As drive member 104 advances, drive member 104 also drives knife pusher 256 in the direction indicated by arrows "B" due to the coupling of tab 104a of drive member 104 with slot 256a of knife pusher 256.

As staple pusher 128 advances in the direction indicated by arrows "B", fingers 134 of staple pusher 128 advance through staple receiving slots 122 to drive or eject staples 124 out of staple receiving slots 122 through openings 122a, through tissue portions "$T_U$" and "$T_L$" grasped between anvil assembly 140 and staple cartridge 120, and against staple forming pockets 148 of anvil assembly 140 to thereby form staples 124. Staples 124 secure upper and lower tissue portions "$T_U$" and "$T_L$" together.

As knife pusher 256 advances in the direction indicated by arrows "B", knife blade 252 is also advanced distally due to lip 262 of flanged portion 260 engaging knife blade 252. As knife blade 252 is advanced distally, knife edge 254 engages and severs the portion of upper and lower tissue portions "$T_U$" and "$T_L$" (FIG. 10) disposed radially inward of staple cartridge 120, thereby forming an anastomosis donut "D" (FIG. 11). The anastomosis donut "D" may be positioned coaxially about locking sleeve 200 of anvil assembly 140.

With reference again to FIG. 11, as knife pusher 256 is advanced in the direction indicated by arrows "B", the at least one recess 266 in the distal end surface 260 engages legs 216 of locking sleeve 200 to drive locking sleeve 200 in the direction indicated by arrows "B". As locking sleeve 200 is driven in the direction "B", e.g., distally, the legs 216 of locking sleeve 200 are driven distally out of the recesses 110b of inner cylindrical portion 110 to release the legs 216 of locking sleeve 200 from the recesses 110b. Once released, the legs 216 of locking sleeve 200 are driven inward in a direction "C" (FIG. 11) against central portion 190 of anvil sleeve 160 due to the bias of legs 216.

Figure 11A:
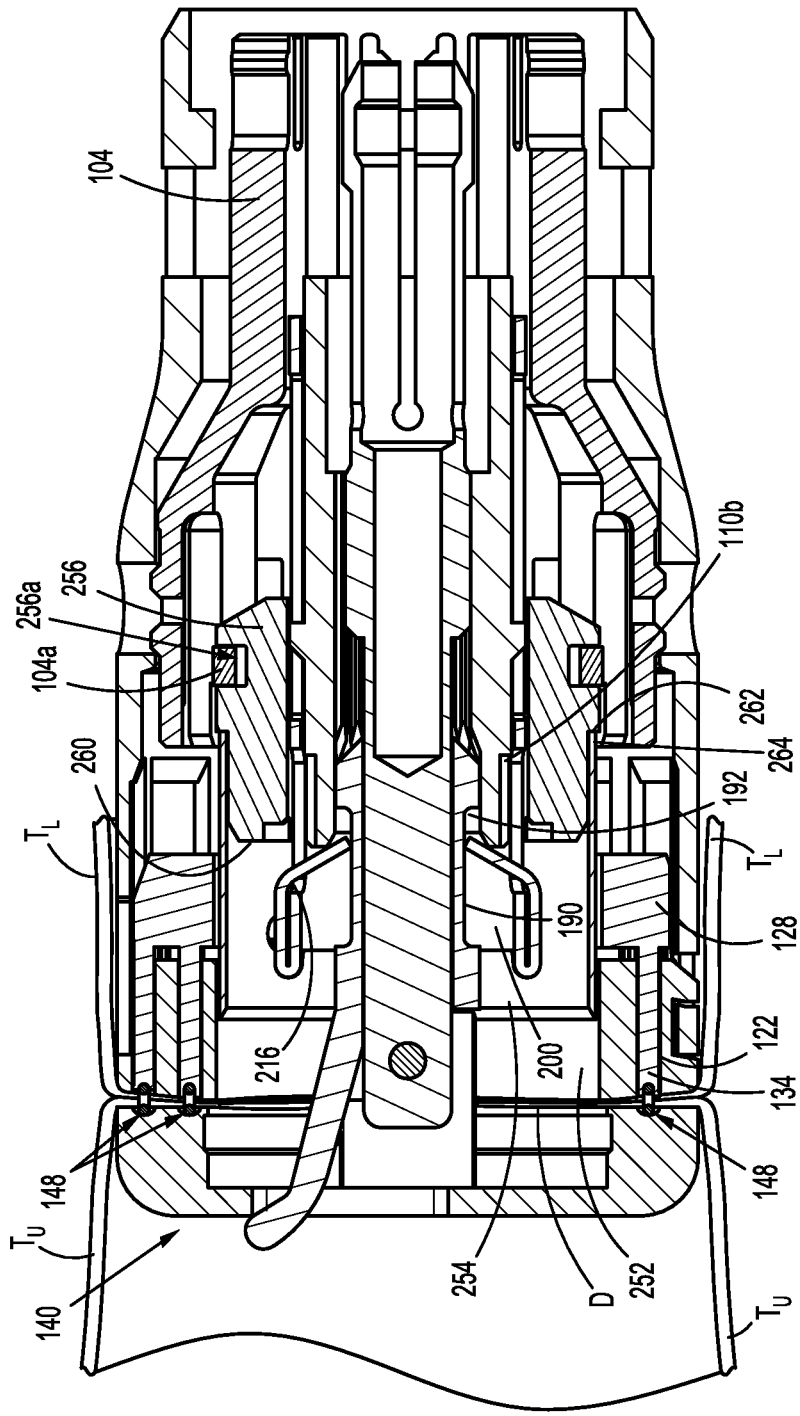
FIG. 11A is a side, cross-sectional view of the tool assembly of FIG. 11, illustrating the drive member and knife pusher being returned to the initial position after firing.

With reference now to FIG. 11A, after knife blade 252 severs upper and lower tissue portions "$T_U$" and "$T_L$" and locking sleeve 200 engages anvil sleeve 160, drive member 104 is retracted. As drive member 104 retracts, knife pusher 256 is also retracted proximally to the initial position due to the coupling of tab 104a of drive member 104 with the slot 256a of knife pusher 256. Staple pusher 128 remains at least partially in the advanced position and locking sleeve 200 remains engaged to anvil sleeve 160 in at least a partially advanced position.

Referring now to FIGS. 12-14, after drive member 104 is retracted, knob 18 is actuated to un-approximate anvil assembly 140 with respect to staple cartridge 120. As anvil assembly un-approximates relative to staple cartridge 120, anvil sleeve 160 is maintained in the first position relative to anvil assembly 140 due to protrusions 182 (FIG. 6) of base portion 174 being engaged to the recess 184 (FIG. 6) of anvil base 152. As anvil sleeve 160 is advanced distally with anvil assembly 140, legs 216 of locking sleeve 200 slide along central portion 190 to engage lip 192. Once legs 216 engage lip 192, locking sleeve 200 also advances distally. As locking sleeve 200 is advanced distally, tabs 110a of inner cylindrical portion 110 slide along slots 222 of locking sleeve 200 until tabs 110a engage the proximal ends 222a of their respective slots 222.

Referring now to FIGS. 13 and 14, once tabs 110a engage the proximal ends 222a of their respective slots, further distal advancement of locking sleeve 200 is inhibited and, due to the engagement of the second ends 216b of legs 216 with the lip 192 of anvil sleeve 160, further distal advancement of anvil sleeve 160 is also inhibited. As anvil assembly 140 is further un-approximated relative to staple cartridge 120, the protrusions 182 (FIG. 13) of base portion 174 disengage from the recess 184 (FIG. 6) of anvil base 152 to allow the anvil assembly 140 to transition to the second position relative to anvil sleeve 160 such that elongate portion 162 becomes spaced from anvil base 152. As elongate portion 162 becomes spaced from anvil base 152, the protrusions 170 of anvil base 152 are released from recesses 172 to allow anvil head 142 to tilt.

Figure 15:
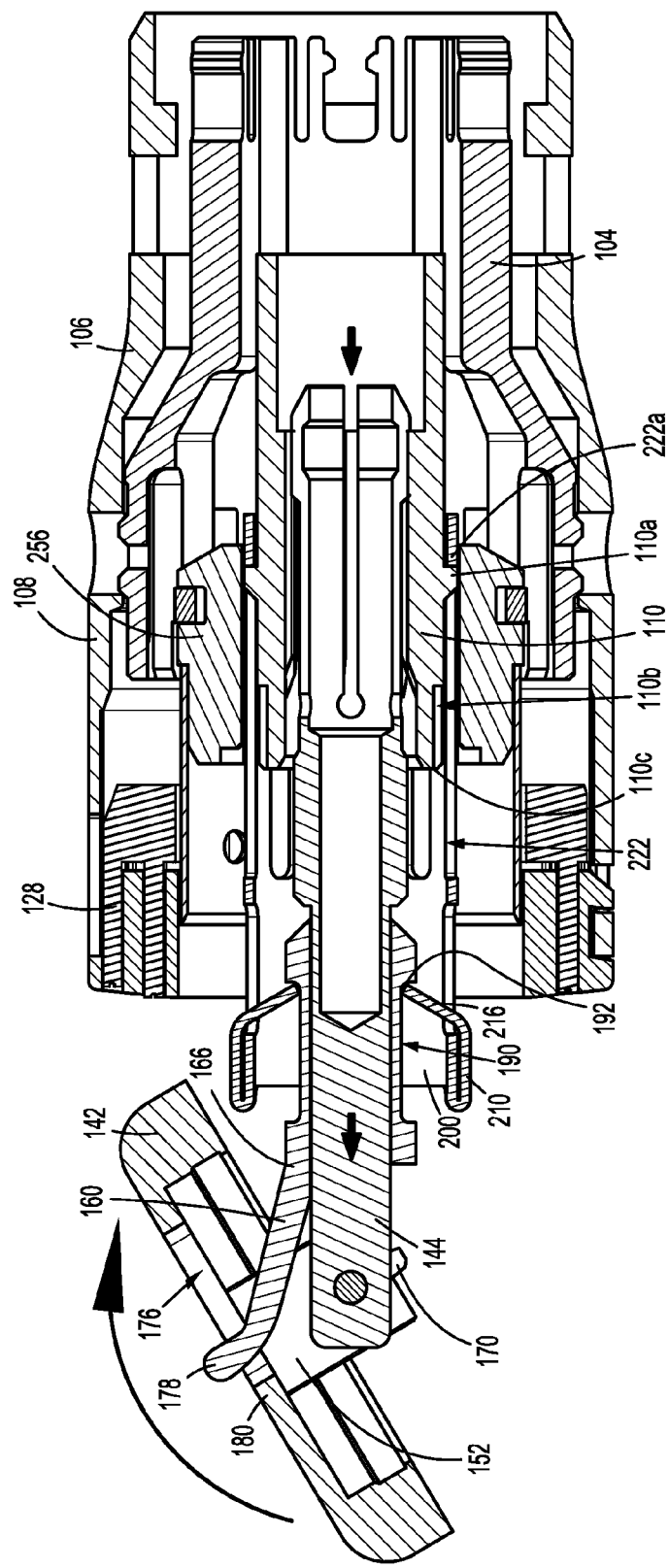
FIG. 15 is a side, cross-sectional view of the tool assembly of FIGS. 13 and 14, illustrating the anvil head in a tilted position.
Figure 16:
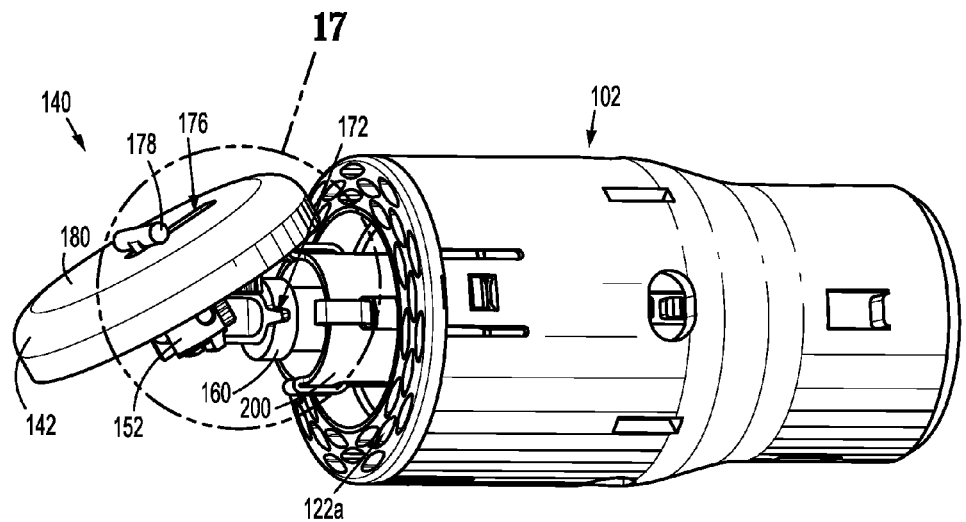
FIG. 16 is a perspective view of the tool assembly of FIG. 15.
Figure 17:
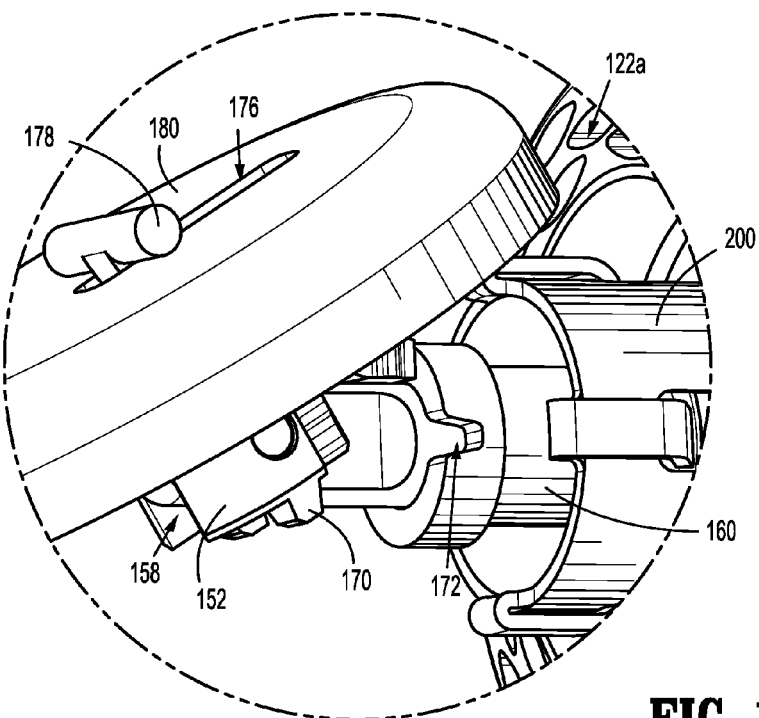
FIG. 17 is an enlarged view of the area of detail 17 of FIG. 16.

Referring now to FIGS. 15-17, as anvil assembly 140 is further un-approximated, flange 178 of anvil head 142 engages the top surface 180 of anvil head 142 to draw down or cause anvil head 142 to tilt to the final tilted condition due to the mechanical force applied by flange 178 on anvil sleeve 160. Once in the final tilted condition, surgical stapling device 10 is ready for removal from the surgical site.

It is contemplated that individual features of the above described embodiments may be combined without departing from the scope of the present disclosure. For example, any of the above embodiments may include the necessary structures or elements to perform either single stroke staple/forming and cutting or separate multi-stroke staple forming and cutting while still utilizing the appropriate locking member and sliding sleeve. In addition, any of the above embodiments may alternatively include a powered actuation system as described above.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical stapling device for joining tissue portions, comprising:
    a handle assembly;
    an elongate body extending from the handle assembly;
    a cartridge assembly supported on a distal end of the elongate body, the cartridge assembly including a staple cartridge containing a plurality of surgical staples in an annular array;
    an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue disposed therebetween, the head of the anvil assembly transitionable between a first condition, where a tissue contacting surface of the head is substantially perpendicular to the shaft, and a second condition, where the tissue contacting surface of the head is tilted relative to the shaft; and
    an anvil sleeve including an elongate portion slidably disposed about the shaft of the anvil assembly and an arm extending from the elongate portion, the anvil sleeve being transitionable between a first position, where the elongate portion of the anvil sleeve is engaged to the head of the anvil assembly to secure the head in the first condition, and a second position, where the elongate portion of the anvil sleeve is spaced from head of the anvil assembly to allow the head to transition to the second condition, the arm being configured to engage the anvil head when the anvil sleeve transitions to the second position to transition the anvil head to the second condition;

wherein the arm includes at least one protrusion configured for releasable engagement with a recess of the anvil head to inhibit transitioning of the anvil sleeve relative to the anvil assembly from the first position to the second position.

2. A surgical stapling device for joining tissue portions, comprising:

a handle assembly;

an elongate body extending from the handle assembly;

a cartridge assembly supported on a distal end of the elongate body, the cartridge assembly including a staple cartridge containing a plurality of surgical staples in an annular array;

an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue disposed therebetween, the head of the anvil assembly transitionable between a first condition, where a tissue contacting surface of the head is substantially perpendicular to the shaft, and a second condition, where the tissue contacting surface of the head is tilted relative to the shaft; and an anvil sleeve including an elongate portion slidably disposed about the shaft of the anvil assembly and an arm extending from the elongate portion, the anvil sleeve being transitionable between a first position, where the elongate portion of the anvil sleeve is releasably secured to the head of the anvil assembly to secure the head in the first condition, and a second position, where the elongate portion of the anvil sleeve is disengaged and spaced from the head of the anvil assembly to allow the head to transition to the second condition, the arm being configured to engage the anvil head when the anvil sleeve transitions to the second position to transition the anvil head to the second condition;

wherein the cartridge assembly includes a locking sleeve, the locking sleeve translatable relative to the anvil sleeve to engage the anvil sleeve when the anvil assembly is in the second position, the locking sleeve configured to disengage the anvil sleeve from the anvil assembly during transition of the anvil assembly from the second position to the first position, the locking sleeve including at least one tab configured for engagement with a lip of the elongate portion of the anvil sleeve to disengage the anvil sleeve from the anvil assembly during transition of the anvil assembly from the second position to the first position; and wherein the elongate portion includes a distal portion, a central portion and a proximal portion, the central portion being recessed relative to the distal and proximal portions such that the central portion and proximal portion define the lip at the interface therebetween.

3. A surgical stapling device for joining tissue portions, comprising:

a handle assembly;

an elongate body extending from the handle assembly;

a cartridge assembly supported on a distal end of the elongate body, the cartridge assembly including a staple cartridge containing a plurality of surgical staples in an annular array;

an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue disposed therebetween, the head of the anvil assembly transitionable between a first condition, where a tissue contacting surface of the head is substantially perpendicular to the shaft, and a second condition, where the tissue contacting surface of the head is tilted relative to the shaft; and an anvil sleeve including an elongate portion slidably disposed about the shaft of the anvil assembly and an arm extending from the elongate portion, the anvil sleeve being transitionable between a first position, where the elongate portion of the anvil sleeve is releasably secured to the head of the anvil assembly to secure the head in the first condition, and a second position, where the elongate portion of the anvil sleeve is disengaged and spaced from the head of the anvil assembly to allow the head to transition to the second condition, the arm being configured to engage the anvil head when the anvil sleeve transitions to the second position to transition the anvil head to the second condition;

wherein the cartridge assembly includes a locking sleeve, the locking sleeve translatable relative to the anvil sleeve to engage the anvil sleeve when the anvil assembly is in the second position, the locking sleeve configured to disengage the anvil sleeve from the anvil assembly during transition of the anvil assembly from the second position to the first position, the locking sleeve including at least one tab configured for engagement with a lip of the elongate portion of the anvil sleeve to disengage the anvil sleeve from the anvil assembly during transition of the anvil assembly from the second position to the first position, the at least one tab being biased inward toward the elongate portion of the anvil sleeve.

4. A surgical stapling device for joining tissue portions, comprising:

a handle assembly;

an elongate body extending from the handle assembly;

a cartridge assembly supported on a distal end of the elongate body, the cartridge assembly including a staple cartridge containing a plurality of surgical staples in an annular array;

an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue disposed therebetween, the head of the anvil assembly transitionable between a first condition, where a tissue contacting surface of the head is substantially perpendicular to the shaft, and a second condition, where the tissue contacting surface of the head is tilted relative to the shaft; and an anvil sleeve including an elongate portion slidably disposed about the shaft of the anvil assembly and an arm extending from the elongate portion, the anvil sleeve being transitionable between a first position, where the elongate portion of the anvil sleeve is releasably secured to the head of the anvil assembly to secure the head in the first condition, and a second position, where the elongate portion of the anvil sleeve is disengaged and spaced from the head of the anvil assembly to allow the head to transition to the second condition, the arm being configured to engage the anvil head when the anvil sleeve transitions to the second position to transition the anvil head to the second condition;

wherein the cartridge assembly includes a locking sleeve, the locking sleeve translatable relative to the anvil sleeve to engage the anvil sleeve when the anvil assembly is in the second position, the locking sleeve configured to disengage the anvil sleeve from the anvil assembly during transition of the anvil assembly from the second position to the first position, the locking sleeve including at least one tab configured for engagement with a lip of the elongate portion of the anvil sleeve to disengage the anvil sleeve from the anvil assembly during transition of the anvil assembly from the second position to the first position; and wherein each tab includes an arcuate portion extending from a distal end of the locking member, a longitudinal portion extending proximally from the arcuate portion and a leg extending from the longitudinal portion through an opening of the locking sleeve.

5. A surgical stapling device for joining tissue portions, comprising:
a handle assembly;
an elongate body extending from the handle assembly;
a cartridge assembly supported on a distal end of the elongate body, the cartridge assembly including a staple cartridge containing a plurality of surgical staples in an annular array;
an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue disposed therebetween, the head of the anvil assembly transitionable between a first condition, where a tissue contacting surface of the head is substantially perpendicular to the shaft, and a second condition, where the tissue contacting surface of the head is tilted relative to the shaft; and
an anvil sleeve including an elongate portion slidably disposed about the shaft of the anvil assembly and an arm extending from the elongate portion, the anvil sleeve being transitionable between a first position, where the elongate portion of the anvil sleeve is releasably secured to the head of the anvil assembly to secure the head in the first condition, and a second position, where the elongate portion of the anvil sleeve is disengaged and spaced from the head of the anvil assembly to allow the head to transition to the second condition, the arm being configured to engage the anvil head when the anvil sleeve transitions to the second position to transition the anvil head to the second condition;
wherein the cartridge assembly includes a locking sleeve, the locking sleeve translatable relative to the anvil sleeve to engage the anvil sleeve when the anvil assembly is in the second position, the locking sleeve configured to disengage the anvil sleeve from the anvil assembly during transition of the anvil assembly from the second position to the first position, the locking sleeve including at least one tab configured for engagement with a lip of the elongate portion of the anvil sleeve to disengage the anvil sleeve from the anvil assembly during transition of the anvil assembly from the second position to the first position; and
wherein the at least one tab is disposed in a recess of the cartridge assembly when the locking sleeve is in a first, proximal position, the at least one tab being configured to release from the recess of the cartridge assembly and engage the lip of the anvil sleeve when the locking sleeve is transitioned to at least one subsequent distal position.

6. A surgical stapling device according to claim 5, wherein the cartridge assembly includes a knife pusher operably coupled to the handle assembly and configured to distally advance a knife blade to sever tissue disposed radially inward of the staple cartridge upon actuation of the handle assembly.

7. A surgical stapling device according to claim 6, wherein the knife pusher includes at least one recess at a distal end thereof, the at least one recess being configured to engage a respective tab of the locking sleeve upon distal advancement of the knife pusher to advance the locking sleeve distally from the first, proximal position to the at least one subsequent distal position.

8. A method of use for a surgical stapling device having an anvil assembly with a pivoting head, the method comprising the steps of:
inserting the surgical stapling device into an opening in a body;
positioning the surgical stapling device within the body such that a portion of tissue is disposed between an anvil assembly and a cartridge assembly of the surgical stapling device;
translating the anvil assembly from a first position, where the anvil assembly is spaced from the cartridge assembly, to a second position, where the anvil assembly approximated relative to the cartridge assembly to clamp the tissue therebetween;
translating a staple pusher relative to the cartridge assembly to urge a plurality of fasteners disposed in the cartridge assembly through the tissue towards the anvil assembly;
translating a locking sleeve of the cartridge assembly relative to an anvil sleeve of the anvil assembly such that a portion of the locking sleeve engages the anvil sleeve;
translating the anvil assembly from the second position to the first position, the anvil sleeve of the anvil assembly disengaging from the anvil assembly due to the engagement of the locking sleeve with the anvil sleeve to allow the head to pivot;

engaging an arm of the anvil sleeve against the head of the anvil assembly to pivot the head of the anvil assembly; and withdrawing the surgical stapling device from the body;

wherein translating the locking sleeve relative to the anvil sleeve includes translating a knife pusher of the cartridge assembly relative to the locking sleeve to engage the locking sleeve and translate the locking sleeve relative to the anvil sleeve.

* * * * *